(12) United States Patent
Harvey et al.

(10) Patent No.: US 11,615,803 B2
(45) Date of Patent: *Mar. 28, 2023

(54) METHODS, APPARATUS AND SYSTEMS FOR BIOMETRIC PROCESSES

(71) Applicant: Cirrus Logic International Semiconductor Ltd., Edinburgh (GB)

(72) Inventors: Thomas Ivan Harvey, Edinburgh (GB); John Paul Lesso, Edinburgh (GB); William Erik Sherwood, Edinburgh (GB); Fredrick D. Geiger, Edinburgh (GB)

(73) Assignee: Cirrus Logic, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/507,886

(22) Filed: Oct. 22, 2021

(65) Prior Publication Data

US 2022/0084541 A1 Mar. 17, 2022

Related U.S. Application Data

(63) Continuation of application No. 17/065,179, filed on Oct. 7, 2020, now Pat. No. 11,189,300.

(Continued)

(51) Int. Cl.
*H04R 29/00* (2006.01)
*G10L 25/51* (2013.01)
(Continued)

(52) U.S. Cl.
CPC .............. *G10L 25/51* (2013.01); *A61B 5/117* (2013.01); *G02B 27/017* (2013.01); *G06F 3/012* (2013.01);
(Continued)

(58) Field of Classification Search
CPC ....... G10L 25/51; A61B 5/117; G02B 27/017; G06F 3/012; H04R 1/023; H04R 1/1041
See application file for complete search history.

(56) References Cited

U.S. PATENT DOCUMENTS 10,362,385 B1 7/2019 Di Censo et al.
10,506,336 B1 12/2019 Lesso
(Continued)

FOREIGN PATENT DOCUMENTS

| EP | 3337183 A1 | 6/2018 |
|---|---|---|
| WO | 2018129242 A1 | 7/2018 |
| WO | 2019008389 A1 | 1/2019 |

OTHER PUBLICATIONS

International Search Report and Written Opinion of the International Searching Authority, International Application No. PCT/GB2020/052312, dated Nov. 18, 2020.

*Primary Examiner* — Simon King
(74) *Attorney, Agent, or Firm* — Jackson Walker L.L.P.

(57) ABSTRACT

A method for use in a biometric process, comprising: with a headset in a known acoustic environment, applying an acoustic stimulus at a first transducer of the headset; receiving a response signal at a second transducer of the headset, the response signal comprising a component of the acoustic stimulus reflected at an obstacle in the acoustic path of the first transducer; determining a condition of the headset based on the response signal; and performing the biometric process based on the determined condition.

20 Claims, 10 Drawing Sheets

Related U.S. Application Data

(60) Provisional application No. 62/945,986, filed on Dec. 10, 2019, provisional application No. 62/930,214, filed on Nov. 4, 2019.

(51) Int. Cl.
| | | |
|---|---|---|
| *A61B 5/117* | (2016.01) | |
| *H04R 1/02* | (2006.01) | |
| *H04R 1/10* | (2006.01) | |
| *H04R 3/04* | (2006.01) | |
| *G02B 27/01* | (2006.01) | |
| *G06F 3/01* | (2006.01) | |
| *H04R 25/00* | (2006.01) | |

(52) U.S. Cl.
CPC ............ *H04R 1/023* (2013.01); *H04R 1/1041* (2013.01); *H04R 3/04* (2013.01); *H04R 25/654* (2013.01)

(56) References Cited

U.S. PATENT DOCUMENTS

| | | | |
|---|---|---|---|
| 2014/0233744 A1* | 8/2014 | Risberg | H04R 3/002 381/61 |
| 2014/0311499 A1* | 10/2014 | Lee | G10K 11/17861 128/866 |
| 2017/0214994 A1* | 7/2017 | Gadonniex | H04R 1/105 |
| 2017/0332186 A1* | 11/2017 | Riggs | H04S 7/301 |
| 2018/0190259 A1* | 7/2018 | Woelfl | G10K 11/17815 |
| 2019/0012444 A1 | 1/2019 | Lesso et al. | |
| 2019/0012445 A1 | 1/2019 | Lesso et al. | |
| 2019/0012446 A1 | 1/2019 | Lesso | |
| 2019/0012447 A1 | 1/2019 | Lesso | |
| 2019/0012448 A1 | 1/2019 | Lesso | |
| 2019/0230426 A1 | 7/2019 | Chun | |
| 2019/0294769 A1 | 9/2019 | Lesso | |
| 2019/0295554 A1 | 9/2019 | Lesso | |
| 2020/0184057 A1 | 6/2020 | Mukund | |
| 2020/0297252 A1* | 9/2020 | Pietrobon | A61B 5/7405 |
| 2020/0314526 A1 | 10/2020 | Lee et al. | |

* cited by examiner

METHODS, APPARATUS AND SYSTEMS FOR BIOMETRIC PROCESSES

The present disclosure is a continuation of U.S. Nonprovisional patent application Ser. No. 17/065,179, filed Oct. 7, 2020, which claims priority to U.S. Provisional Patent Application Ser. No. 62/945,986, filed Dec. 10, 2019, and U.S. Provisional Patent Application Ser. No. 62/930,214, filed Nov. 4, 2019, each of which is incorporated by reference herein in its entirety.

TECHNICAL FIELD

Embodiments of the disclosure relate to methods, apparatus and systems for biometric processes, and particularly to methods, apparatus and systems for biometric processes involving the measured response of a user's ear to an acoustic stimulus.

BACKGROUND

It is known that the acoustic properties of a user's ear, whether the outer parts (known as the pinna or auricle), the ear canal or both, differ substantially between individuals and can therefore be used as a biometric to identify the user. One or more loudspeakers or similar transducers positioned close to or within the ear generate an acoustic stimulus, and one or more microphones similarly positioned close to or within the ear detect the acoustic response of the ear to the acoustic stimulus. One or more features may be extracted from the response signal, and used to characterize an individual.

For example, the ear canal is a resonant system, and therefore one feature which may be extracted from the response signal is the resonant frequency of the ear canal. If the measured resonant frequency (i.e. in the response signal) differs from a stored resonant frequency for the user, a biometric algorithm coupled to receive and analyse the response signal may return a negative result. Other features of the response signal may be similarly extracted and used to characterize the individual. For example, the features may comprise one or more mel frequency cepstral coefficients. More generally, the transfer function between the acoustic stimulus and the measured response signal (or features of the transfer function) may be determined, and compared to a stored transfer function (or stored features of the transfer function) which is characteristic of the user.

A problem associated with ear biometric systems is the susceptibility of a measured biometric response to change over time due to deterioration of one or more components of the devices, such as headsets, used for biometric processes (e.g. enrolment and authentication). This problem can be exacerbated since the signal to noise ratio of a measured response signal from the user's ear is typically quite low as the biometric features of the signal are relatively weak. Deterioration of device components can cause the signal to noise ratio to further reduce.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each of the appended claims.

SUMMARY

According to an aspect of the disclosure, there is provided a method for use in a biometric process, comprising: with a headset in a known acoustic environment, applying an acoustic stimulus at a first transducer of the headset; receiving a response signal at a second transducer of the headset, the response signal comprising a component of the acoustic stimulus reflected at an obstacle in the acoustic path of the first transducer; determining a condition of the headset based on the response signal; and updating performing the biometric process based on the determined condition.

The known acoustic environment may be a charging case of the headset or an ear of a user or may be free field, i.e. with the headset in another known acoustic environment (e.g. substantial silence).

The obstacle may comprises a transducer grille, cover, or the like. The condition may comprises a blockage in the acoustic path.

Determining the condition may comprise comparing the response signal to a template response signal. The template response signal may represents an optimal condition of the acoustic path or some previous condition of the acoustic path.

Performing the biometric process may comprises conditioning a further response signal received at the second transducer after the response signal based on the determined condition of the headset; and performing the biometric process on the conditioned further response signal.

The conditioning may comprise subtracting a difference between the response signal and the template response signal from the further response signal to generate the conditioned future response signal. Conditioning may comprise filtering the further response signal.

Determining the condition may further comprise extracting one or more features of the response signal. Comparing the response signal to the template signal comprises comparing each of the extracted features with a corresponding template feature, the corresponding template features representing the optimal condition of the acoustic path or the previous condition of the acoustic path.

Performing the biometric process may comprise reducing a threshold for matching a measured biometric response to a template response.

Additionally or alternatively, performing the biometric process comprises disabling the biometric process.

Performing the biometric process comprises selecting a biometric template response for use in the biometric process. The selected biometric template may be a biometric template trained on data relating to the determined condition of the acoustic path.

Performing the biometric process may comprise increasing a number of biometric inputs to the biometric process. Biometric inputs may comprise one or more of an ear biometric, a finger biometric, and a face biometric.

The biometric process may be one of biometric enrolment and biometric authentication. Biometric enrolment may comprises generating and storing a unique model of a user of the headset. Biometric authentication may comprise comparing the response signal to a template for the user.

The first transducer may be a loud speaker. The second transducer may be a microphone. The first transducer and the second transducer may in some embodiments be the same transducer.

According to an aspect of the disclosure, there is provided an apparatus, comprising processing circuitry and a non-transitory machine-readable which, when executed by the processing circuitry, cause the apparatus to: with a headset in a known acoustic environment, apply an acoustic stimulus by a first transducer of the headset; receive a response signal at a second transducer of the headset, the response signal comprising a component of the acoustic stimulus reflected at an obstacle in the acoustic path of the first transducer; determine a condition of the headset based on the response signal; and perform or update the biometric process based on the determined condition.

The apparatus may comprise the first transducer; and the second transducer. The first transducer may be a loud speaker. The second transducer may be a microphone.

According to an aspect of the disclosure, there is provided an electronic device, comprising the apparatus described above.

According to an aspect of the disclosure, there is provided a non-transitory machine-readable medium storing instructions which, when executed by one or more processors, cause an electronic apparatus to: with a headset in a known acoustic environment, apply an acoustic stimulus at a first transducer of the headset; receive a response signal at a second transducer of the headset, the response signal comprising a component of the acoustic stimulus reflected at an obstacle in the acoustic path of the first transducer; determine a condition of the headset based on the response signal; and perform or update the biometric process based on the determined condition.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting example only with reference to the accompanying drawings, in which.

DESCRIPTION OF EMBODIMENTS

As noted above, ear biometric data may be acquired by the generation of an acoustic stimulus, and the detection of an acoustic response of the ear to the acoustic stimulus. One or more features may be extracted from the response signal, and used to characterize the individual.

The acoustic stimulus may be generated and the response measured using a personal audio device. As used herein, the term "personal audio device" is any electronic device which is suitable for, or configurable to, provide audio playback substantially to only a single user. Some examples of suitable personal audio devices are shown in FIGS. 1a to 1e.

Figure 1A:
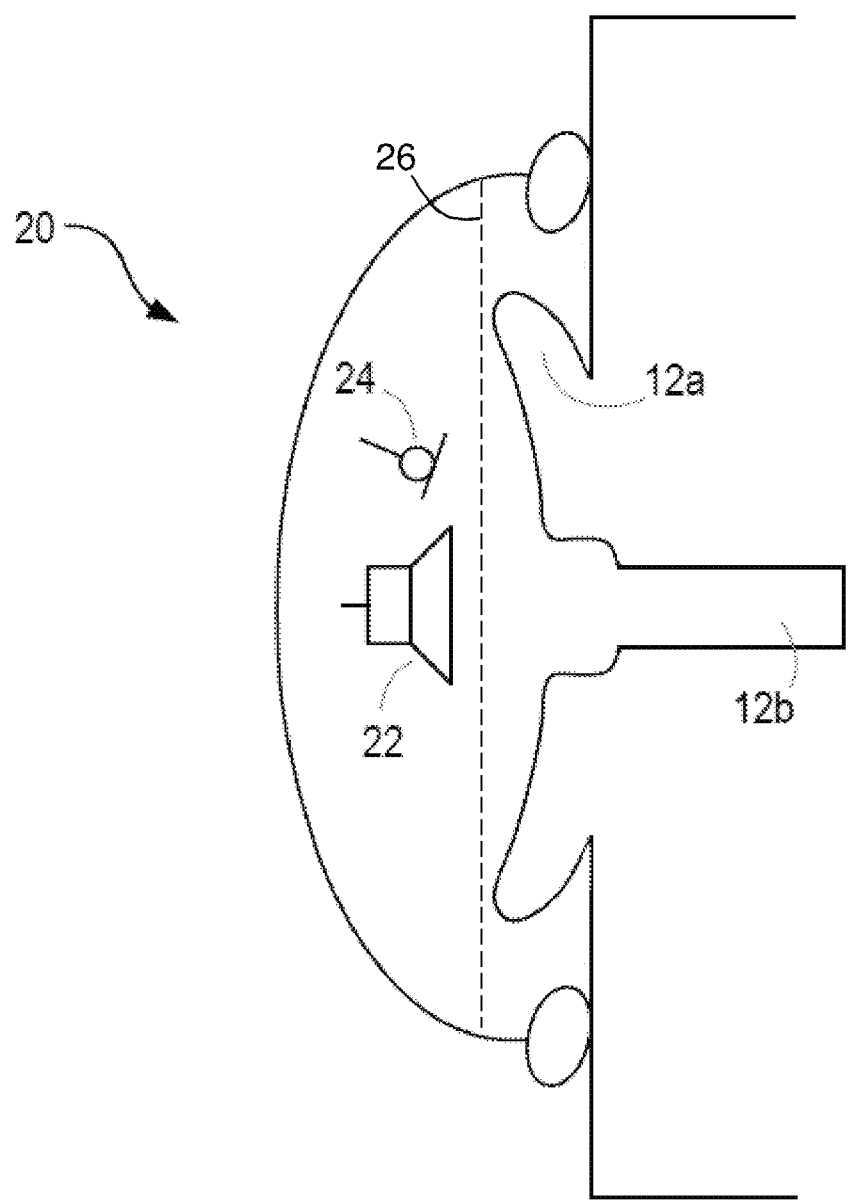
FIGS. 1a to 1e are schematic diagrams of example personal audio devices.

FIG. 1a shows a schematic diagram of a user's ear, comprising the (external) pinna or auricle 12a, and the (internal) ear canal 12b. A personal audio device 20 comprising a circum-aural headphone is worn by the user over the ear. The headphone comprises a shell which substantially surrounds and encloses the auricle 12a, so as to provide a physical barrier between the user's ear and the external environment. Cushioning or padding may be provided at an edge of the shell, so as to increase the comfort of the user, and also the acoustic coupling between the headphone and the user's skin (i.e. to provide a more effective barrier between the external environment and the user's ear).

The headphone comprises one or more loudspeakers 22 positioned on an internal surface of the headphone, and arranged to generate acoustic signals towards the user's ear and particularly the ear canal 12b. The headphone further comprises one or more microphones 24, also positioned on the internal surface of the headphone, arranged to detect acoustic signals within the internal volume defined by the headphone, the auricle 12a and the ear canal 12b. The headphone further comprises a grille 26 between the speaker 22 and the ear which may allow sound to pass but prevents ingress of dirt, moisture and other matter that may cause damage to components of the headphone.

The headphone may be able to perform active noise cancellation, to reduce the amount of noise experienced by the user of the headphone. Active noise cancellation operates by detecting a noise (i.e. with a microphone), and generating a signal (i.e. with a loudspeaker) that has the same amplitude as the noise signal but is opposite in phase. The generated signal thus interferes destructively with the noise and so lessens the noise experienced by the user. Active noise cancellation may operate on the basis of feedback signals, feedforward signals, or a combination of both. Feedforward active noise cancellation utilizes one or more microphones on an external surface of the headphone, operative to detect the environmental noise before it reaches the user's ear. The detected noise is processed quickly, and the cancellation signal generated so as to match the incoming noise as it arrives at the user's ear. Feedback active noise cancellation utilizes one or more error microphones positioned on the internal surface of the headphone, operative to detect the combination of the noise and the audio playback signal generated by the one or more loudspeakers. This combination is used in a feedback loop, together with knowledge of the audio playback signal, to adjust the cancelling signal generated by the loudspeaker and so reduce the noise. The microphone 24 shown in FIG. 1a may therefore form part of an active noise cancellation system, for example, as an error microphone.

Figure 1B:
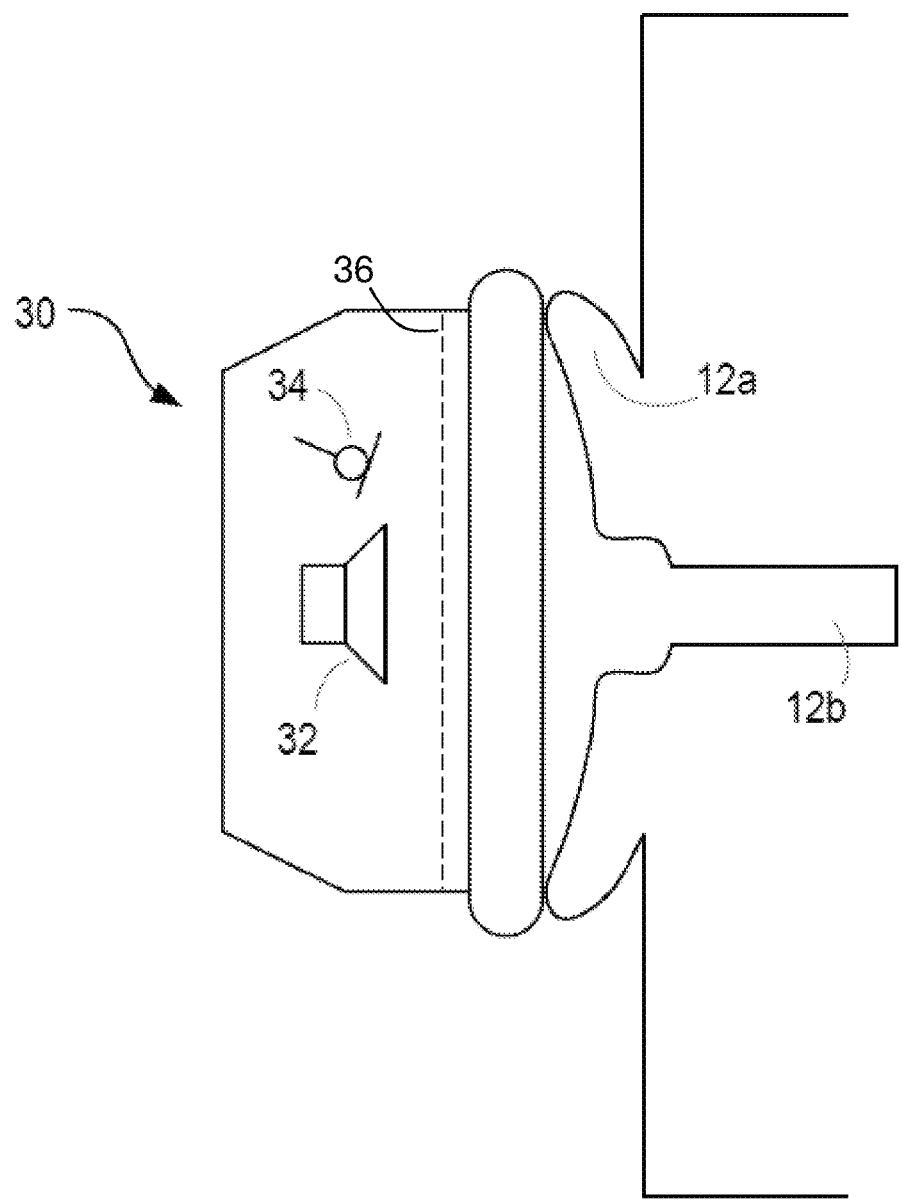

FIG. 1b shows an alternative personal audio device 30, comprising a supra-aural headphone. The supra-aural headphone does not surround or enclose the user's ear, but rather sits on the auricle 12a. The headphone may comprise a cushion or padding to lessen the impact of environmental noise. As with the circum-aural headphone shown in FIG. 1a, the supra-aural headphone comprises one or more loudspeakers 32, one or more microphones 34, and one or more grilles 36. The loudspeaker(s) 32 and the microphone(s) 34 may form part of an active noise cancellation system, with the microphone 34 serving as an error microphone.

Figure 1C:
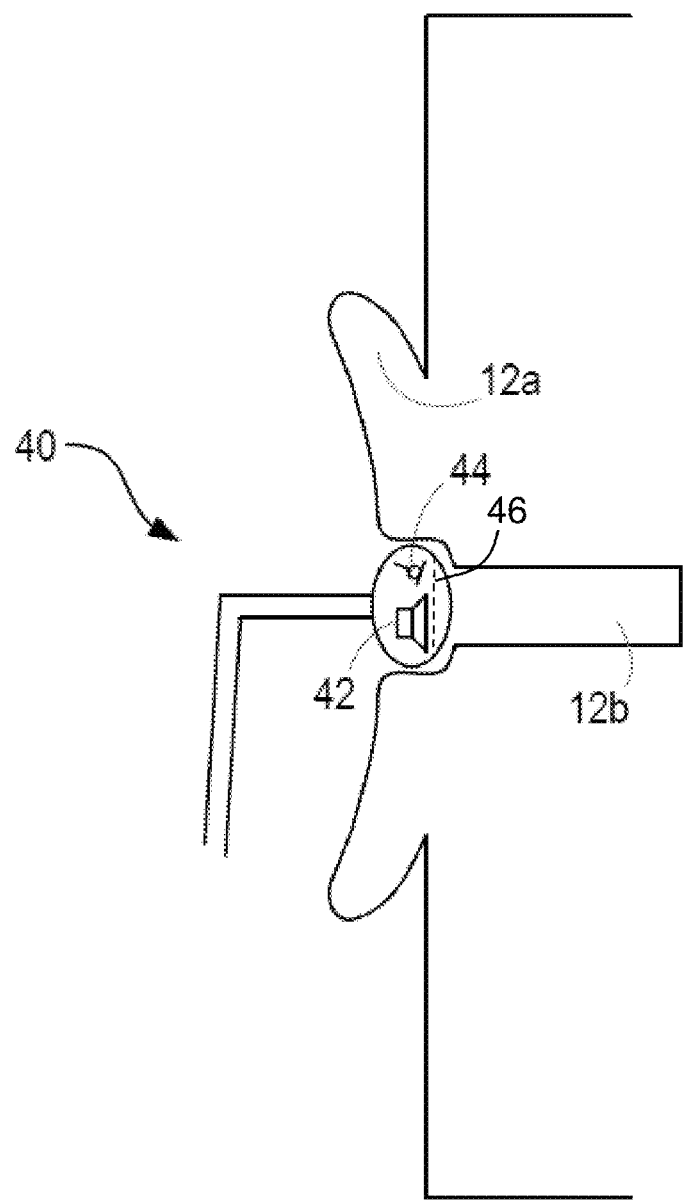

FIG. 1c shows a further alternative personal audio device 40, comprising an intra-concha headphone (or earphone). In use, the intra-concha headphone sits inside the user's concha cavity. The intra-concha headphone may fit loosely within the cavity, allowing the flow of air into and out of the user's ear canal 12b.

As with the devices shown in FIGS. 1a and 1b, the intra-concha headphone comprises one or more loudspeakers 42 and one or more microphones 44, which may form part of an active noise cancellation system, together with one or more grilles 46.

Figure 1D:
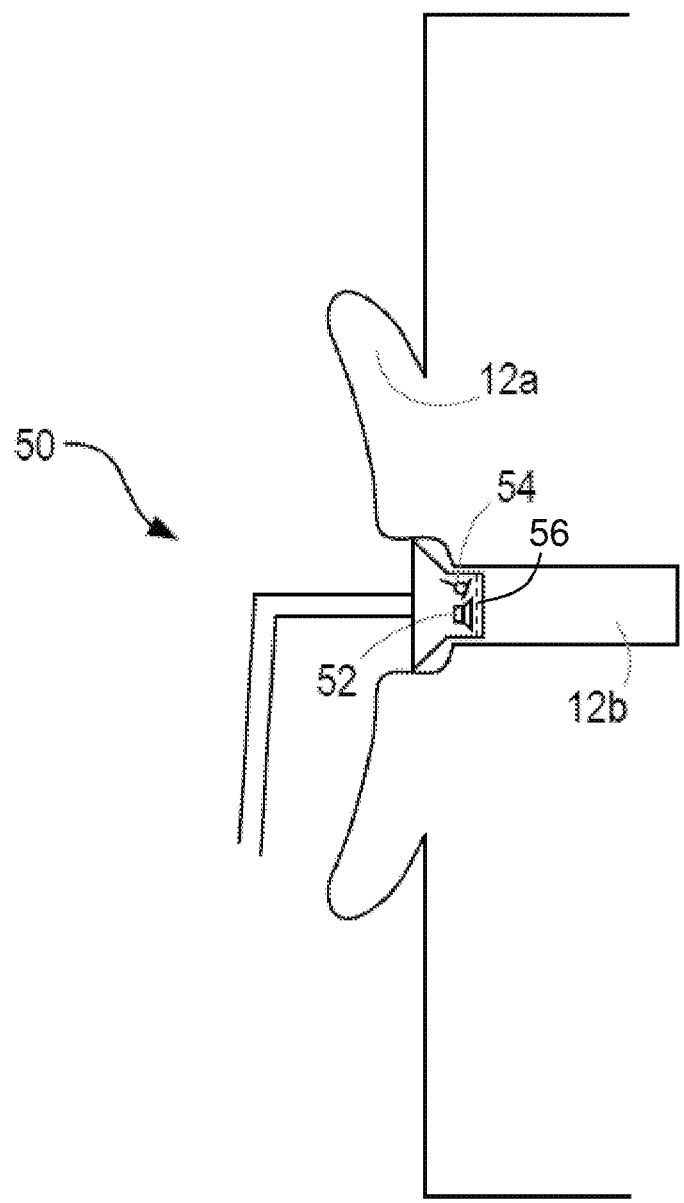

FIG. 1d shows a further alternative personal audio device 50, comprising an in-ear headphone (or earphone), insert headphone, or ear bud. This headphone is configured to be partially or totally inserted within the ear canal 12b, and may provide a relatively tight seal between the ear canal 12b and the external environment (i.e. it may be acoustically closed or sealed). The headphone may comprise one or more loudspeakers 52, one or more microphones 54, and one or more grilles 56, as with the other devices described above, and these components may form part of an active noise cancellation system.

As the in-ear headphone may provide a relatively tight acoustic seal around the ear canal 12b, external noise (i.e. coming from the environment outside) detected by the microphone 54 is likely to be low.

Figure 1E:
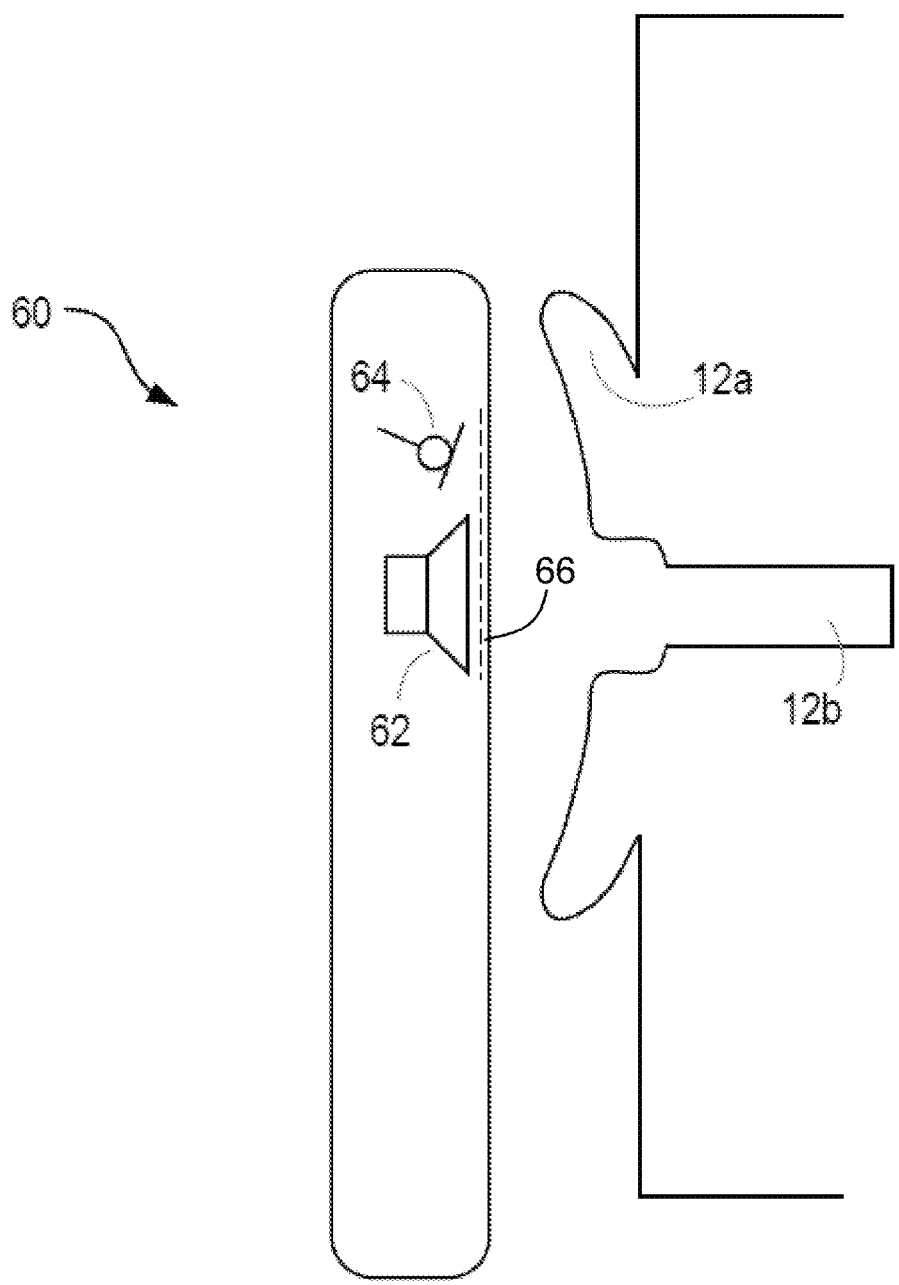

FIG. 1e shows a further alternative personal audio device 60, which is a mobile or cellular phone or handset. The handset 60 comprises one or more loudspeakers 62 for audio playback to the user, and one or more microphones 64 which are similarly positioned, together with one or more grilles 66 for allowing sound to pass into and out of the device 60 whilst preventing ingress of grit, dirt, moisture and other matter which may cause damage to internal components of the device 60.

In use, the handset 60 is held close to the user's ear so as to provide audio playback (e.g. during a call). While a tight acoustic seal is not achieved between the handset 60 and the user's ear, the handset 60 is typically held close enough that an acoustic stimulus applied to the ear via the one or more loudspeakers 62 generates a response from the ear which can be detected by the one or more microphones 64. As with the other devices, the loudspeaker(s) 62 and microphone(s) 64 may form part of an active noise cancellation system.

All of the personal audio devices described above thus provide audio playback to substantially a single user in use. Each device comprises one or more loudspeakers and one or more microphones, which may be utilized to generate biometric data related to the frequency response of the user's ear. The loudspeaker is operable to generate an acoustic stimulus, or acoustic probing wave, towards the user's ear, and the microphone is operable to detect and measure a response of the user's ear to the acoustic stimulus, e.g. to measure acoustic waves reflected from the ear canal or the pinna. The acoustic stimulus may be sonic (for example in the audio frequency range of say 20 Hz to 20 kHz) or ultra-sonic (for example greater than 20 kHz or in the range 20 kHz to 50 kHz) or near-ultrasonic (for example in the range 15 kHz to 25 kHz) in frequency. The acoustic stimulus may have frequency components which span one or more of sonic, ultra-sonic, and near-ultrasonic ranges. In some examples the microphone signal may be processed to measure received signals of the same frequency as that transmitted.

Each of the personal audio devices described above comprises one or more loudspeakers in addition to one or more microphones. However, in some embodiments, the one or more speakers may be used both to generate an acoustic stimulus and as an input device to detect and measure a response of the user's ear to the acoustic stimulus, e.g. to measure acoustic waves reflected from the ear canal or the pinna. For example, the response of the user's ear may be estimated by measuring the current through the loudspeaker or transducer. Alternatively, for example, the response of the user's ear may be estimated by calculating the impedance of the loudspeaker or transducer. In such cases, the one or more microphones may be omitted.

Another biometric marker may comprise otoacoustic noises emitted by the cochlear in response to the acoustic stimulus waveform. The otoacoustic response may comprise a mix of the frequencies in the input waveform. For example if the input acoustic stimulus consists of two tones at frequencies f1 and f2, the otoacoustic emission may include a component at frequency 2*f1−f2. The relative power of frequency components of the emitted waveform has been shown to be a useful biometric indicator. In some examples therefore the acoustic stimulus may comprise tones of two or more frequencies and the amplitude of mixing products at sums or differences of integer-multiple frequencies generated by otoacoustic emissions from the cochlear may be measured. Alternatively, otoacoustic emissions may be stimulated and measured by using stimulus waveforms comprising fast transients, e.g. clicks.

Depending on the construction and usage of the personal audio device, the measured response may comprise user-specific components, i.e. biometric data relating to the auricle 12a, the ear canal 12b, or a combination of both the auricle 12a and the ear canal 12b. For example, the circum-aural headphones shown in FIG. 1a will generally acquire data relating to the auricle 12a and potentially also the ear canal 12b. The insert headphones shown in FIG. 1d will generally acquire data relating only to the ear canal 12b.

One or more of the personal audio devices described above (or rather, the microphones within those devices) may be operable to detect bone-conducted voice signals from the user. That is, as the user speaks, sound is projected away from the user's mouth through the air. However, acoustic vibrations will also be carried through part of the user's skeleton or skull, such as the jaw bone. These acoustic vibrations may be coupled to the ear canal 12b through the jaw or some other part of the user's skeleton or skull, and detected by the microphone. Lower frequency sounds tend to experience a stronger coupling than higher frequency sounds, and voiced speech (i.e. that speech or those phonemes generated while the vocal cords are vibrating) is coupled more strongly via bone conduction than unvoiced speech (i.e. that speech or those phonemes generated while the vocal cords are not vibrating). The in-ear headphone 50 may be particularly suited to detecting bone-conducted speech owing to the tight acoustic coupling around the ear canal 12b.

All of the devices shown in FIGS. 1a to 1e and described above may be used to implement aspects of the disclosure.

Figure 2:
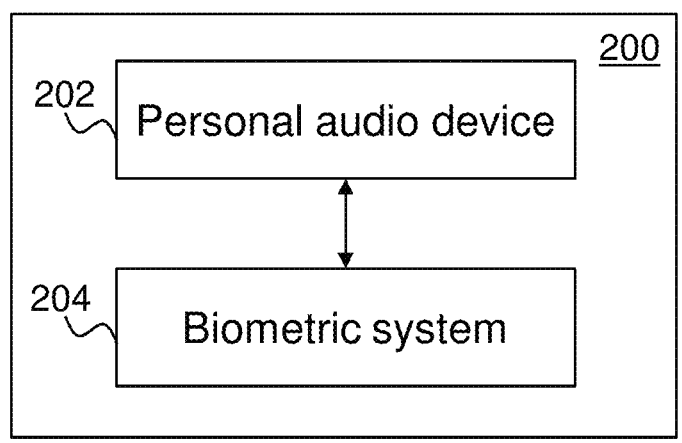
FIG. 2 is a block diagram of an arrangement according to embodiments of the present disclosure.

FIG. 2 shows an arrangement 200 according to embodiments of the disclosure. The arrangement 200 comprises a personal audio device 202 and a biometric system 204. The personal audio device 202 may be any device which is suitable for, or configurable to provide audio playback to substantially a single user. The personal audio device 202 generally comprises one or more loudspeakers, and one or more microphones which, in use, are positioned adjacent to or within a user's ear. The personal audio device 202 may be wearable, and comprise headphones for each of the user's ears. Alternatively, the personal audio device 202 may be operable to be carried by the user, and held adjacent to the user's ear or ears during use. The personal audio device 202 may comprise headphones or a mobile phone handset, as described above with respect to any of FIGS. 1a to 1e.

The biometric system 204 is coupled to the personal audio device 202 and operative to control the personal audio device 202 to acquire biometric data which is indicative of the individual using the personal audio device 202.

The personal audio device 202 thus generates an acoustic stimulus for application to the user's ear, and detects or measures the response of the ear to the acoustic stimulus. The measured response corresponds to the reflected signal received at the one or more microphones, with certain frequencies being reflected at higher amplitudes than other frequencies owing to the particular response of the user's ear.

Some examples of suitable biometric processes include biometric enrolment and biometric authentication. Enrolment comprises the acquisition and storage of biometric data which is characteristic of an individual. In the present context, such stored data may be known as an "ear print". Authentication (sometimes referred to as verification or identification) comprises the acquisition of biometric data from an individual, and the comparison of that data to the stored ear prints of one or more enrolled or authorised users. A positive comparison (i.e. a determination that the acquired data matches or is sufficiently close to a stored ear print) results in the individual being authenticated. For example, the individual may be permitted to carry out a restricted action, or granted access to a restricted area or device. A negative comparison (i.e. a determination that the acquired data does not match or is not sufficiently close to a stored ear print) results in the individual not being authenticated. For example, the individual may not be permitted to carry out the restricted action, or granted access to the restricted area or device.

The biometric system 204 may, in some embodiments, form part of the personal audio device 202 itself. Alternatively, the biometric system 204 may form part of an electronic host device (e.g. an audio player) to which the personal audio device 202 is coupled, through wires or wirelessly. In yet further embodiments, operations of the biometric system 204 may be distributed between circuitry in the personal audio device 202 and the electronic host device.

The biometric system 204 may send suitable control signals to the personal audio device 202, so as to initiate the acquisition of biometric data, and receive data from the personal audio device 202 corresponding to the measured response. The biometric system 204 is operable to extract one or more features from the measured response and utilize those features as part of a biometric process.

As mentioned previously, a problem associated with ear biometric systems is the susceptibility of a measured biometric response to change over time due to deterioration of one or more components of the device used for detecting the biometric response. For example, ingress of dirt in the speaker grille of a headphone, such as those shown in FIGS. 1a to 1e, can lead to a change in the characteristics of sound output from the headphone as well as signals received at an internal microphone in the headphone.

Figure 3:
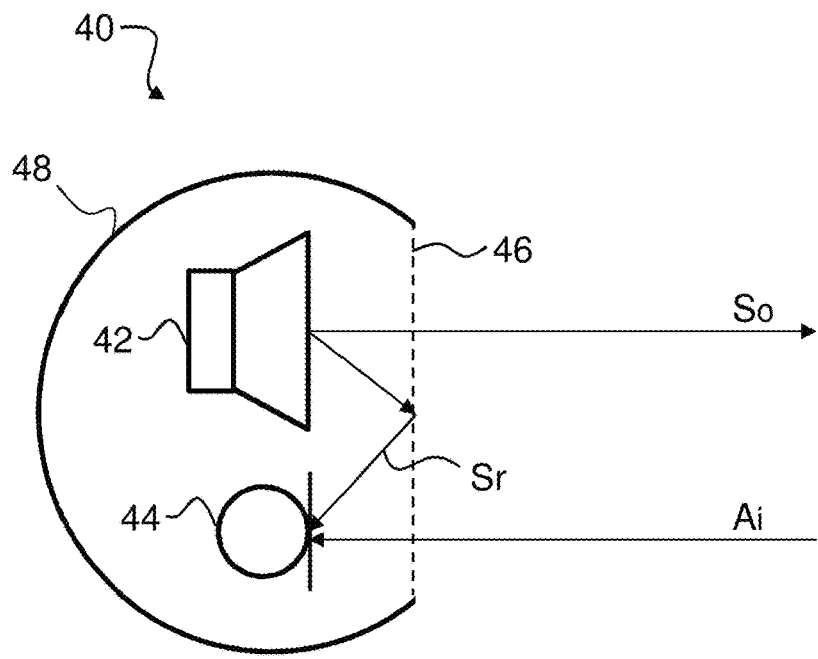
FIG. 3 is a block diagram of a system according to embodiments of the present disclosure.

FIG. 3 is a more detailed schematic diagram of the personal audio device 40 described above. The following explanation is described with reference to the personal audio device 40, but equally applies to any of the personal audio devices described above or herein which each comprise components, such as grilles, which may be susceptible to deterioration due to ingress of dirt, wax and other matter.

As mentioned above, the device 40 comprises a loudspeaker 42 and a microphone 44 housed within a headphone shell 48. The grille 46 is provided in the headphone shell 48 and configured to allow sound to pass therethrough whilst preventing or mitigating ingress of dirt, moisture and the like into the shell 48. Arrows $S_o$ represents a component of sound originating from the loudspeaker 42 which is transmitted through the grille 46 to the outside of the audio device 40. Arrow $S_r$ represents a component of sound generated by the speaker 42 which is reflected from the inside surface of the grille 46 and is incident at the microphone 44. Arrow Ai represents the component of ambient sound outside of the shell 48 transmitted through the grille 46 which is incident at the microphone 44.

As foreign matter (dirt, wax, skin etc.) builds up on and in the grille 46, the energy of components So, Ai of sound transmitted through the grille 46 and reaching the microphone 44 decrease due to increased absorption at the grille 46. Additionally, the energy of the component Sr reflected at the internal surface of the grille 46 may increase.

Figure 4:
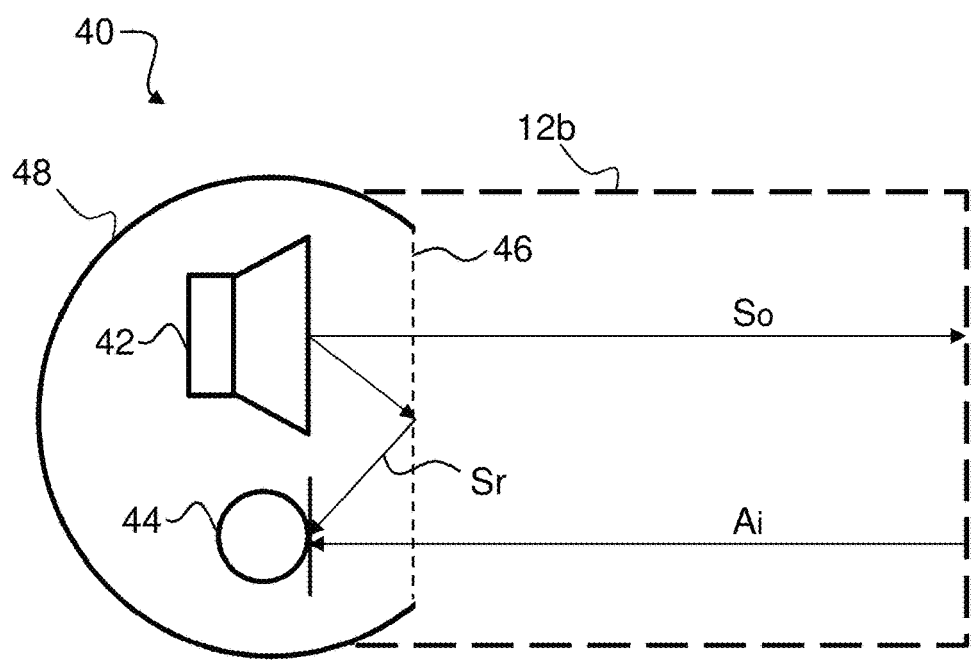
FIG. 4 is a flow diagram of a process according to embodiments of the present disclosure.

FIG. 4 shows the device 40 positioned at the entrance of the ear canal 12b. Again, it will be appreciated that, with ingress of dirt and other matter in the grille 46, a measured response of the ear canal 12b at the microphone 44 to an acoustic stimulus output at the speaker 42 may change over time. Additionally, the characteristics of optoacoustic noise emitted by the cochlear in response to an acoustic stimulus detected at the microphone 44 may also change since components of such noise may be attenuated.

Figure 5:
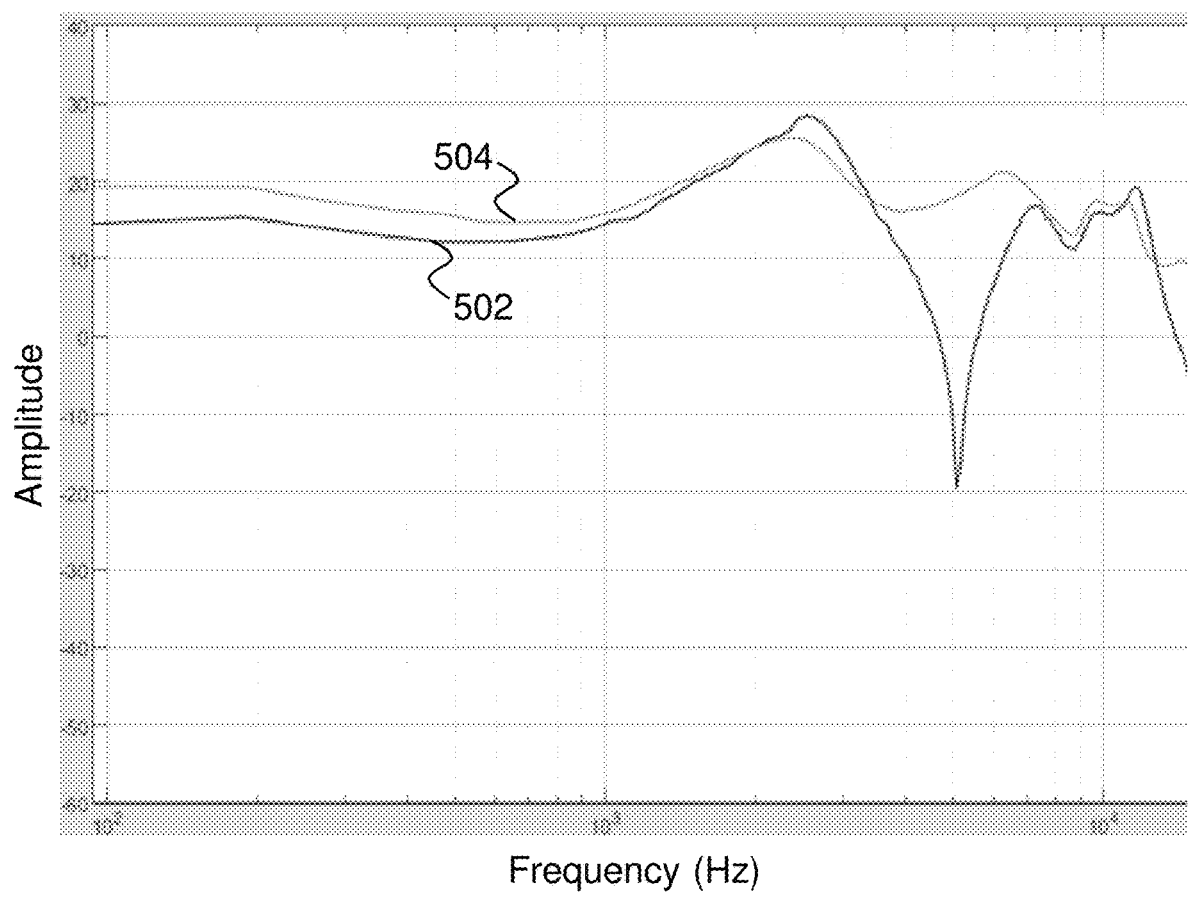
FIG. 5 graphically illustrates frequency responses of a microphone to white noise output at a speaker in the presence of a clean grille and a dirty grille with a device positioned at an ear canal, according to embodiments of the present disclosure.

FIG. 5 graphically illustrates the frequency responses 402, 404 of the microphone 44 to white noise output at the speaker 42 in the presence of a clean grille 46 (line 502) and a dirty grille 46 (line 504) with the device 40 positioned at the ear canal 12b. Referring first to line 502, it can be seen that a large "notch" (reduction in amplitude) can be seen between about 3 kHz and about 7 kHz in the signal received at the microphone 44. This "notch" is dependent on the characteristics of the ear canal 12b or external acoustic path and thus can be used as a feature in ear biometrics. Referring then to line 504 in comparison, a comparative increase in amplitude of the response 404 can be seen between about 3 kHz and about 7 kHz with ingress of dirt and was on and in the grille 46. This increase in amplitude is caused by an increase in reflection of sound from the internal surface of the grille due to the deteriorating condition. Referring to FIG. 4, the change in the reflected component Sr accounts for this noise which substantially removes the notch at the detriment of biometric processes. Thus, a change in condition of the grille 46 can substantially affect a measured response detected at the microphone 44 and thus affect the accuracy and security of any biometric process performed using such measurements.

In view of the above, embodiments of the present disclosure provide methods and systems to account for the deterioration of elements in the acoustic path of transducers of audio devices by determining one or more characteristics of signals received at a transducer of such devices in response to an acoustic stimulus. For example, embodiments of the present disclosure may output an acoustic stimulus from a speaker and measure a response signal at a microphone. The response signal and/or one or more characteristics thereof may then be analysed to determine a condition of elements in the acoustic path of the device. Based on that determination, one or more biometric processes used to enrol or authenticate a user of the device may be performed, adjusted or updated in one or more ways to account for the condition or a change in the condition, such as a deterioration of the condition of the element causing a change in a measured response to the acoustic stimulus.

Examples of the elements include, but are not limited to physical elements such as a speaker grille or cover, an acoustic port, an acoustic channel and the like. Examples of a condition of such elements include, but are not limited to a level of build-up or ingress of dirt or wax or any other matter which may attenuate sound travelling to and from the transducer(s).

Figure 6:
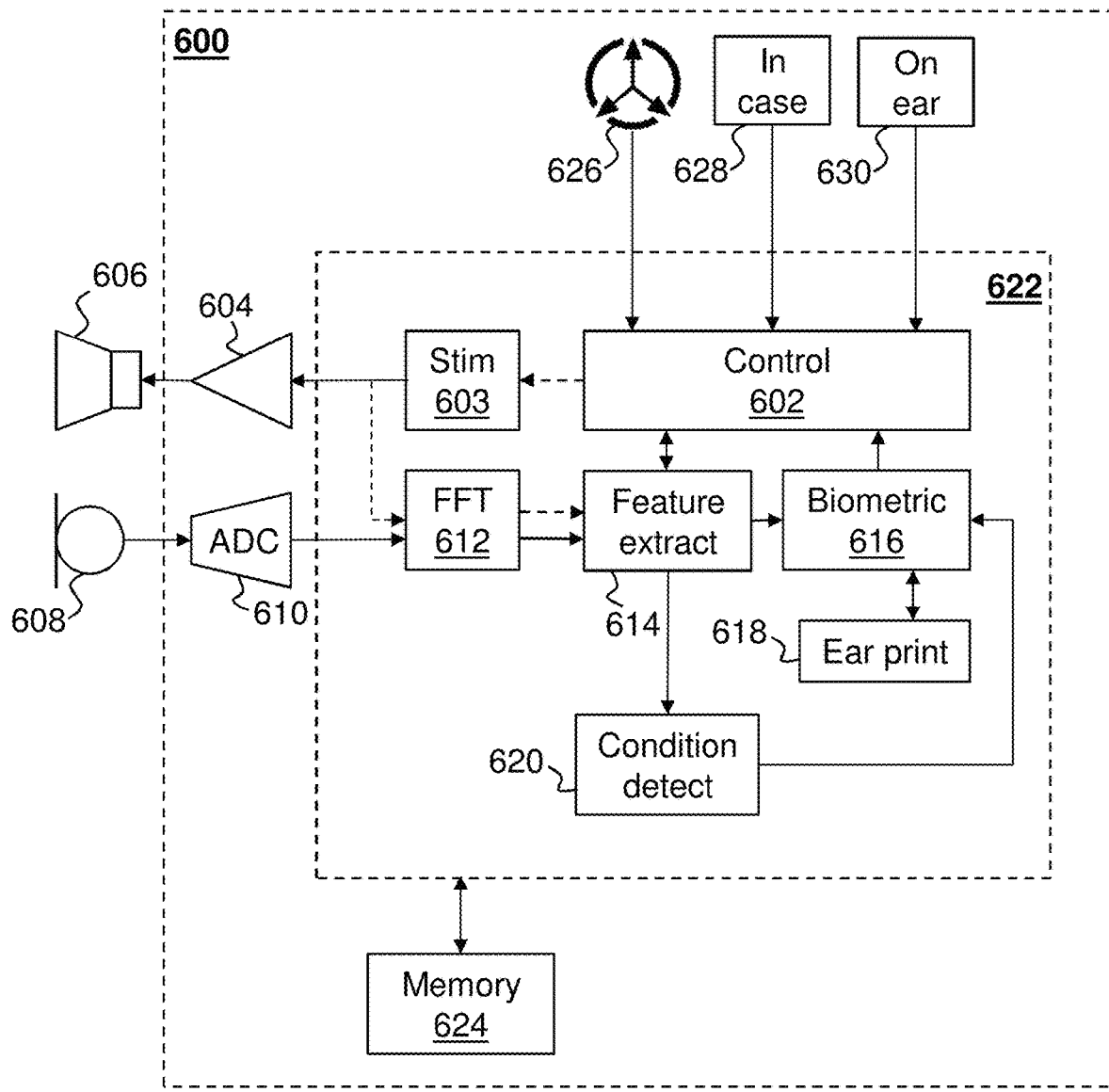
FIG. 6 shows a system according to embodiments of the disclosure.

FIG. 6 shows a system 600 according to embodiments of the disclosure.

The system 600 comprises processing circuitry 622, which may comprise one or more processors, such as a central processing unit or an applications processor (AP), or a digital signal processor (DSP).

The one or more processors may perform methods as described herein on the basis of data and program instructions stored in memory 624. Memory 624 may be provided as a single component or as multiple components or co-integrated with at least some of processing circuitry 622. Specifically, the methods described herein may be performed in processing circuitry 622 by executing instructions that are stored in non-transient form in the memory 624, with the program instructions being stored either during manufacture of the system 600 or personal audio device 202 or by upload while the system 600 or device 602 is in use.

The processing circuitry 622 comprises a stimulus generator module 603 which is coupled directly or indirectly to an amplifier 604, which in turn is coupled to a transducer 606. The transducer 606 and a microphone 608 may form part of a personal audio device, such as the personal audio devices 20, 30, 40, 50, 60 described above with reference to FIGS. 1a to 1e. In other embodiments the transducer 606 may act both as a speaker for generating sound and a microphone or inductor for generating signals from sound incident thereon.

The stimulus generator module 603 generates an electrical audio signal and provides the electrical audio signal to the amplifier 604, which amplifies it and provides the amplified signal to the transducer 606. The transducer 606 generates a corresponding acoustic signal which is output to the user's ear (or ears). In alternative embodiments, the amplifier 604 may form part of the stimulus generator module 603.

As noted above, when the transducer 606 and microphone 608 are positioned at an ear entrance of the user, the audio signal may be output to all or a part of the user's ear (i.e. the auricle 12a or the ear canal 12b of the user as described with reference to FIGS. 1a to 1e). The audio signal is reflected off the ear, and the reflected signal (or echo signal) is detected and received by the microphone 608. The reflected signal thus comprises data which is characteristic of the individual's ear, and suitable for use as a biometric. When the transducer 606 and the microphone 608 are positioned, instead of at the ear, in an acoustic enclosure such as a charging case for one of the personal audio devices 20, 30, 40, 50, 60 described above with reference to FIGS. 1a and 1e, the audio signal is reflected off the internal walls and features of the acoustic enclosure and such reflections may thus comprise data which is characteristic of the enclosure. When the transducer 606 and the microphone 608 are positioned, instead of at the ear or in an acoustic enclosure, in free field, i.e. positioned on a table or other surface in the open, there are no physical barriers for the audio signal to be reflected off outside of the device. An absence of reflected sound incident at the microphone 608 is characteristic of this free field condition.

In any of the above scenarios (ear, enclosure or free field), in addition to any reflections either from the ear or from features of an acoustic enclosure, the audio signal may also be reflected off features internal to the device in which the transducer 606 is positioned. Such features may include obstacles (e.g. a speaker grille) in the acoustic path of the transducer. As such, reflected components of the signal may comprise data which is characteristic of these obstacles (e.g. a condition of the speaker grille etc.).

It will thus be appreciated that if the acoustic environment in which the transducer 606 and microphone 608 resides is known, then the condition of any obstacles in the acoustic path can be estimated based on characteristics of the signal received at the microphone 608.

The reflected signal is passed from the microphone 608 to an analogue-to-digital converter (ADC) 610, where it is converted from the analogue domain to the digital domain. In alternative embodiments the microphone 608 may be a digital microphone and produce a digital data signal (which does not therefore require conversion to the digital domain).

The signal is detected by the microphone 608 in the time domain. However, the features extracted for the purposes of biometric processing and condition estimation may be in the frequency domain (in that it is the frequency response of the user's ear, the enclosure, or the obstacles which is generally characteristic). In which case, the system 600 may comprise a Fourier transform module 612, which converts the reflected signal to the frequency domain. For example, the Fourier transform module 612 may implement a fast Fourier transform (FFT).

The transformed signal is then passed to a feature extract module 614, which extracts one or more features of the transformed signal for use in both a biometric process (e.g. biometric enrolment, biometric authentication, etc.) and a condition detection process. For example, the feature extract module 614 may extract the resonant frequency of the user's ear or the acoustic enclosure or the internal features of the audio device in which the transducer is located. For example, the feature extract module 614 may extract one or more mel frequency cepstral coefficients. Alternatively, the feature extract module 614 may determine a frequency response at one or more predetermined frequencies, or across one or more ranges of frequencies. The frequency response may be of the user's ear, an acoustic enclosure (e.g. charging case), or of free field in combination with the internals of a headphone shell. To extract such features, the acoustic stimulus generated at the stimulus generator module 603 is also provided to the feature extract module 614, optionally via the Fourier transform module 612, depending on whether the stimulus generator module 603 outputs the acoustic stimulus in the time or frequency domain. By providing the acoustic stimulus to the feature extract module 614, a comparison can be made between the acoustic stimulus and the response to that acoustic stimulus received at the microphone 608.

For characterisation of the condition of elements in the acoustic path of the transducer 606 and microphone 608, the feature extract module 614 may calculate an impedance or reflectance of one or more features in the acoustic path, such as a speaker grille.

To aid the feature extraction module 614 in determining the various extracted features discussed above, the system 600 may further comprise an accelerometer 626 comprised in or associated with a headphone into which the transducer 606 and the microphone 608 are incorporated. The control module 602 may receive one or more inputs from the accelerometer 626 which may in turn be used to determine an orientation of the headphone which may correspond to the headphone being placed on a surface in free field. The control module 602 may further comprise one or both of an in-case detect module 628 and an on-ear detect module 630. The in-case detect module 628 may be configured to detect that the personal audio device 202 into which transducer 606 and microphone 608 are incorporated is housed with an associated acoustic enclosure, such as a charging case. The on-ear detect module 630 may be configured to detect when or whether the personal audio device 202, in particular the transducer 606 is inserted in or located in proximity to the ear. The control module 602 may receive as inputs indications of a free-field condition, an in-case condition or an on-ear condition and provide these to the feature extract module 614. In turn, the feature extract module 614 may extract one or more features based on where the environment in which the transducer 606 and microphone 608 are.

Optionally, where the personal audio device 202 comprises multiple microphones, for example additional microphone(s) other than the microphone 608 shown in FIG. 6, signals derived from those additional microphone(s) may be provided to the feature extract module 614 in a similar manner to that described with reference to the microphone 608 shown in FIG. 6. Such derived signal(s) may be used as a reference signal(s), for example to detect excessive noise and/or to assist in feature extraction, biometric processes and/or condition detection, particularly if an acoustic path exists between the microphone 608 and the additional microphone(s).

Extracted feature(s) pertaining to biometrics may be passed to a biometric module 616, which performs a biometric process on them. For example, the biometric module 616 may perform a biometric enrolment, in which the extracted features (or parameters derived therefrom) are stored as part of biometric data 618 which is characteristic of the individual (i.e. as an ear print). The biometric data 618 may be stored within the system 600 or remote from the system 600 (and accessible securely by the biometric module 616). In another example, the biometric module 616 may perform a biometric authentication, and compare the one or more extract features to corresponding features in a stored ear print 618 (or multiple stored ear prints) for authorised users. Again, the stored ear print 618 may be stored within the system 600 or remote from the system 600 (and accessible securely by the biometric module 616).

The biometric module 616 generates a biometric result (which may be the successful or unsuccessful generation of an ear print, as well as successful or unsuccessful authentication) and outputs the result to the control module 602.

In addition to being passed to the biometric module 616, extracted feature(s) may also be passed to a condition detect module 620 which in other embodiments may be implemented by the biometric module 616. The condition detect module 620 may store condition data comprising extracted features (or parameters derived therefrom) which are characteristic of the audio device 202 in one or more states of condition in one or more known acoustic environments. As noted above, known acoustic environments may include an acoustic enclosure, such as a charging case, an ear of a user and free field, the audio device 40 positioned on a surface in the open. Example states of condition include a new condition or some condition of the audio device 40 (and its components) in the past. This condition data may be stored within the system 600 or remotely accessible by the condition detect module 620.

To determine a condition of audio device 40, the condition detect module 620 may compare the one or more extract features to corresponding reference features previously extracted or determined. The reference features may have been extracted by the feature extract module 614 during a previous biometric process or condition detect process. Additionally or alternatively, the reference features may be extracted during a baseline calibration measurement made at the time of production or refurbishment of the personal audio device 202. Additionally, or alternatively, the reference features may be features determined during modelling of the personal audio device 202 or otherwise estimated.

The comparison made between the extracted features and reference features may represent a condition of the acoustic path between the transducer 606 and the microphone 608. Based on the comparison, the condition detect module 620 may then determine a condition or one or more components in the acoustic path, such as the speaker grille.

In comparing the extracted features and reference features, the condition detect module 620 may determine a difference between one or more extracted features and a corresponding one or more reference features. If the determined difference exceeds a predetermined threshold, the condition detect module 620 may output an indication to the biometric module 616 indicating a deterioration in the condition of the acoustic path. Such a deterioration may indicate to the biometric module 616 that any features extracted by the feature extract module 614 for use in a biometric process may be affected by an adverse acoustic condition. In response, the biometric module 616 may be configured to perform, update, amend, or otherwise change a biometric process being undertaken to account for the change in condition of the acoustic path.

In addition to or as an alternative to outputting an indication to the biometric module 616 of a deterioration in the condition of the acoustic path, the condition detect module 620 may output the determined difference or comparison between the one or more extracted features and their corresponding reference features to the biometric module 616 and/or the control module 602. Such feature difference(s) or comparison(s) may then be used by the biometric module 616 and/or the control module 602 to cancel noise associated with the deterioration in the condition of the acoustic path. In other words, the determined feature difference(s) may be used to either calibrate the signal derived from the microphone 608 or the features extracted therefrom before such features are used in the biometric process. In doing so, any noise associated with a deterioration of the condition of the acoustic path from the ideal may be substantially removed, thus enabling any biometric process implemented by the biometric module 616 using the extracted features to be implemented without loss of accuracy, security etc.

In some embodiments, based on the comparison between extracted and reference features, the biometric module 616 and/or the control module 602 may be configured to generate one or more parameters of a cancellation filter (not shown) configured to cancel noise associated with the acoustic path condition deterioration. In some embodiments, the cancellation filter may pre-filter the frequency domain signal output from the Fourier transform module 612 to remove noise associated with the deterioration in acoustic path condition. For example, any such filter may be implemented using the feature extract module 614 in the frequency domain. Such a filter may be designed using least mean square filter techniques or other known digital filtering techniques. Any such filtering may be adaptive, such that filter parameters may be updated over time in response to one or more changing conditions of the acoustic path, based on successive comparisons of present extracted features with past or ideal measured or modelled features (reference features). In some embodiments, instead of or in addition to being implemented in the frequency domain, filtration may be implemented in the time domain in a manner known in the art.

Taking the example shown in FIG. 5, such filtering may remove the noise present between 5 kHz and 8 kHz thereby restoring, in the signal derived from the deteriorated acoustic path, the notch present in the frequency response for the clean grille (i.e. the non-deteriorated acoustic path condition).

In addition to or as an alternative to cancellation of noise in the derived signal from the microphone 608 due to a deterioration in acoustic path condition, in some embodiments, in response to detecting an adverse condition in the acoustic path, the biometric module 616 may flag that the output of a biometric process is less reliable. The control module 602 may then disable one or more features associated with the biometric process. The control module 602 may reduce a level of security associated with the biometric process (e.g. authentication).

For example, if the biometric process is used to authenticate a secure task, the control module 602 may indicate that additional secure authentication is required in addition to the biometric process to perform the secure task. The secure task may, for example, be unlocking a phone or tablet, logging into an application or initiating an electronic funds transfer or the like. In some embodiments, if the level of security associated with the biometric process is reduced by the control module 602, an output from the biometric process may still authenticate some tasks but not others, for example unlocking a phone or tablet, but not enabling login to one or more secure applications (such as a banking app).

Additionally or alternatively, in some embodiments, in response to detecting a condition in the acoustic path, the biometric module 616 may replace, augment or otherwise change a model or template used in a biometric process. For example, the biometric module 616 may switch to a different model which may be more robust in the presence of altered acoustic path conditions. The more robust model may be a model trained on data associated with adverse acoustic path conditions (e.g. a dirty speaker grille or the like). For example, the biometric module 616 may be using a plurality of models for a biometric process. In which case, the biometric module 616 may change the weighting of the two or more models, so as to rely more heavily on a model which is more robust to adverse acoustic path conditions.

Additionally or alternatively, in some embodiments, in response to detecting a change in condition in the acoustic path over time, the biometric module 616 may iteratively update one or more models used in a biometric process to enrich the biometric process. Such enrichment may be performed over some or all of the lifetime of the personal audio device 202 so as to track temporal deterioration of the acoustic path, for example due to a build-up of dirt and wax on a speaker grille. Any such enrichment process is preferably accompanied by supporting data from one or more additional authentication processes (e.g. fingerprint, face print, or key code) to support a change in biometric enrolment. In doing so, this mitigates bad actors purposefully augmenting an acoustic path to change biometric enrolment models over time.

In addition to adjusting parameters of a biometric process, a detected change in condition at the condition detect module 620 may also be used to re-calibrate or adjust one or more parameters of active noise cancellation (ANC). For example, ANC may be switched off altogether (e.g. if a complete blockage of the acoustic path is detected) or a different (e.g. less aggressive) filter may be implemented. For example, where the system 600 implements both feedforward and feedback (FB) ANC, in response to detecting an adverse condition in the acoustic path, FB ANC may be switched off.

In addition to adjusting parameters of a biometric process, a detected change in condition at the condition detect module 620 may also be used to adjust one or more characteristics of a personalised equalisation (EQ), e.g. an EQ designed specifically for a user of the personal audio device 202 and the fit of the device 202 to the user's ear.

In addition to adjusting parameters of a biometric process, a detected change in condition at the condition detect module 620 may also be used to adjust parameters of any other hearing augmentation, sidetone or other process carried out on any signals being output to the transducer 606.

It will be appreciated that any of the above techniques for adjusting or updating the biometric process by either cancelling or accounting for a deterioration in the acoustic path condition of the personal device 202 may be performed in any conceivable combination without departing from the scope of the disclosure.

As discussed previously, the control module 602 may control the stimulus generator module 603 to output an acoustic stimulus specifically for use in a biometric process or for condition detection. For example, the control module 602 may be configured to control the stimulus generator module 603 to output an authentication cue notifying a user that authentication is taking place. The control module 602 may adjust the properties of the acoustic stimulus so as to maximise the SNR of the measured response signal. The control module 602 may, for example, control the stimulus generator module 603 to increase the amplitude of the stimulus output to the transducer 606 or otherwise adjust the frequency response of the signal. In other embodiments, an initial estimate of an ear canal response or enclosure response or speaker grille impedance or reflection, based on the response signal received at the microphone 608 to the initial acoustic stimulus, may first be ascertained. Then, the control module 602 may control the stimulus generator module 603 to generate an additional acoustic probe signal/stimulus to confirm or strengthen the initial estimate for the purposes of biometric authentication or enrolment, or condition detection. The biometric module 616 may signal to the control module 602 to adjust and re-apply an acoustic stimulus to the transducer 606 based on a determination in a condition of the acoustic path or a change in such condition over time.

The control module 602 may continue to control the stimulus generator module 603 even while the acoustic stimulus is being applied to the transducer 606. For example, the control module 602 may monitor the extracted features or the response signal itself to determine ongoing properties response signal.

In some embodiments the feature extract module 614 may be designed with foreknowledge of the nature of the stimulus, for example knowing the spectrum of the applied stimulus signal, so that the response or transfer function may be appropriately normalised. In other more suitable embodiments the feature extract module 614 may comprise a second input to monitor the stimulus (e.g. playback music, on-ear detect, a virtual assistant, ANC, hearing augmentation, sidetone, adjusted acoustic stimulus etc.) and hence provide the feature extract module 614 with information about the stimulus signal or its spectrum so that the feature extract module 614 may calculate the transfer function from the acoustic stimulus to measured received signal from the microphone 608 from which it may derive the desired feature parameters. In the latter case, the acoustic stimulus may also pass to the feature extract module 614 via the FFT module 612 (denoted by dotted line in FIG. 6).

Figure 7:
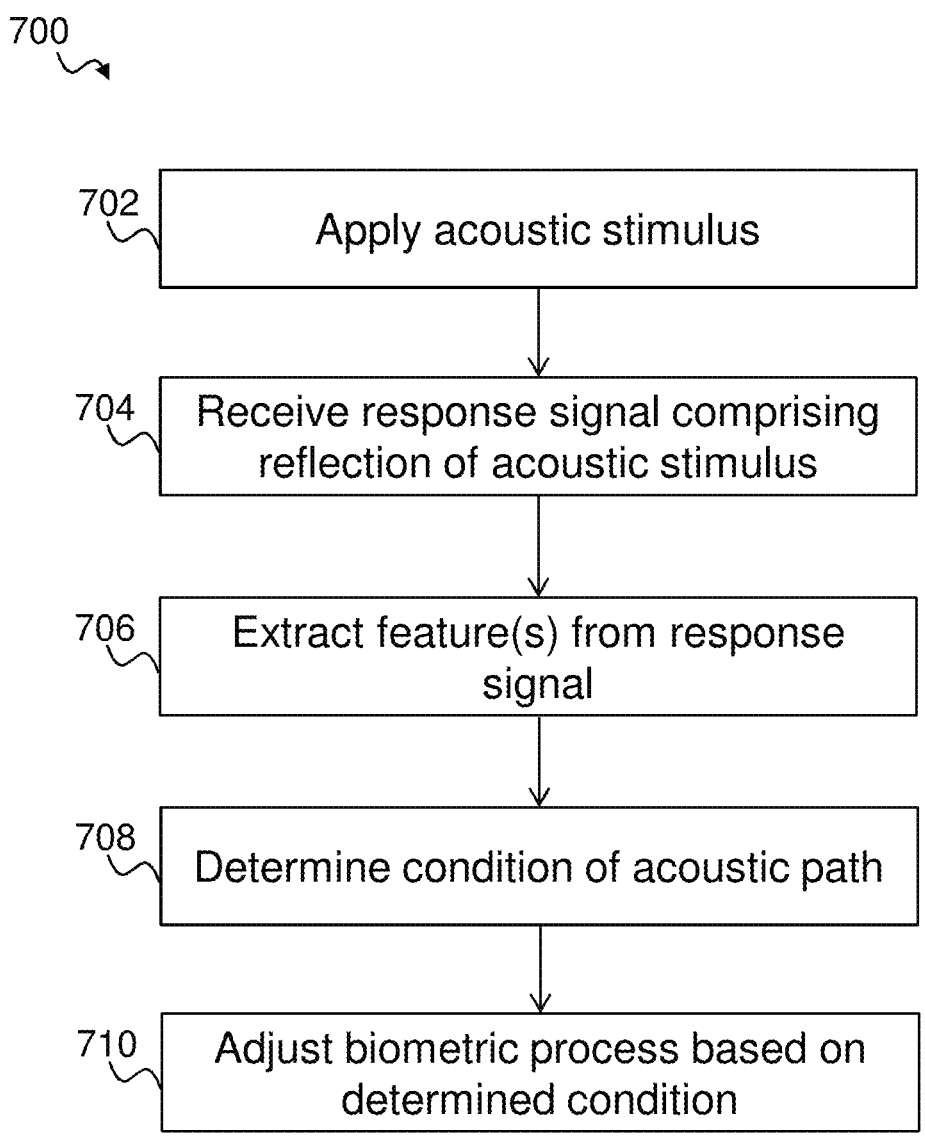
FIG. 7 is a flow diagram of a process which may be performed by the system shown in FIG. 6, according to embodiments of the present disclosure.

FIG. 7 is a flow diagram of a process 700 which may be performed by the system 600 shown in FIG. 6.

At step 702, the system 600 generates and applies an acoustic stimulus using the transducer 606. In some embodiments, the stimulus may be directed towards the outer part of an ear (i.e. the auricle), the ear canal, or both. In other embodiments, the stimulus may be directed to free field. In other embodiments, the stimulus may be directed towards internal features of an acoustic enclosure. The stimulus generator module 603 may generate the acoustic stimulus specifically for condition detection or biometric enrolment or authentication or for any other function, for example, to notify a user that the personal audio device 202 is on the ear or connected, to notify the user that biometric (or other) authentication is imminent, ongoing, or completed, to provide information from a virtual assistant, to deliver audio media to the user's ear, to provide a calibration sound to the user's ear for the purpose of calibrating ANC, to inject sound into the ear for hearing augmentation (e.g. hear through), to inject sidetone into the user's ear.

At step 704, the system 600 receives a response signal to the acoustic stimulus which is incident at the microphone 608 and comprises a component of the acoustic stimulus reflected from features in the acoustic path of the microphone 608.

At step 706, the system 600 extracts, from the response signal, for example as received at the microphone 608, one or more features for use in condition detection process and one or more features for use in a biometric process (e.g. authentication or enrolment). For example, the one or more features may comprise one or more of: a resonant frequency; a frequency response; one or more mel frequency cepstral coefficients, a feature reflectance, and a feature impendence. Biometric enrolment may comprise generating and storing a unique model for the user based on the one or more features. Biometric authentication may comprise comparing the one or more features to a unique model for the user. Condition detection may comprise comparing the one or more features with reference features previously extracted, modelled or estimated.

At step 708, the system 600 determines a condition of the acoustic path of the transducer 606, the microphone 608 or both. The condition may comprise a condition of one or more physical components in the acoustic path, such as a speaker grille. The condition may be a build-up of dirt or wax in the acoustic path or an amount thereof.

At step 710, the system 600, may perform, adjust, update or otherwise augment the biometric process being performed by the biometric module 616 based on the condition of the acoustic path determined at step 708.

Embodiments may be implemented in an electronic, portable and/or battery powered host device such as a smartphone, an audio player, a mobile or cellular phone, a handset. Embodiments may be implemented on one or more integrated circuits provided within such a host device. Embodiments may be implemented in a personal audio device configurable to provide audio playback to a single person, such as a smartphone, a mobile or cellular phone, headphones, earphones, etc. See FIGS. 1a to 1e. Again, embodiments may be implemented on one or more integrated circuits provided within such a personal audio device. In yet further alternatives, embodiments may be implemented in a combination of a host device and a personal audio device. For example, embodiments may be implemented in one or more integrated circuits provided within the personal audio device, and one or more integrated circuits provided within the host device.

It should be understood—especially by those having ordinary skill in the art with the benefit of this disclosure—that the various operations described herein, particularly in connection with the figures, may be implemented by other circuitry or other hardware components. The order in which each operation of a given method is performed may be changed, and various elements of the systems illustrated herein may be added, reordered, combined, omitted, modified, etc. It is intended that this disclosure embrace all such modifications and changes and, accordingly, the above description should be regarded in an illustrative rather than a restrictive sense.

Similarly, although this disclosure makes reference to specific embodiments, certain modifications and changes can be made to those embodiments without departing from the scope and coverage of this disclosure. Moreover, any benefits, advantages, or solutions to problems that are described herein with regard to specific embodiments are not intended to be construed as a critical, required, or essential feature or element.

Further embodiments and implementations likewise, with the benefit of this disclosure, will be apparent to those having ordinary skill in the art, and such embodiments should be deemed as being encompassed herein. Further, those having ordinary skill in the art will recognize that various equivalent techniques may be applied in lieu of, or in conjunction with, the discussed embodiments, and all such equivalents should be deemed as being encompassed by the present disclosure.

The skilled person will recognise that some aspects of the above-described apparatus and methods, for example the discovery and configuration methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high speed integrated circuit Hardware Description Language). As the skilled person will appreciate, the code may be distributed between a plurality of coupled components in communication with one another.

Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

It should be noted that the above-mentioned embodiments illustrate rather than limit the invention, and that those skilled in the art will be able to design many alternative embodiments without departing from the scope of the appended claims or embodiments. The word "comprising" does not exclude the presence of elements or steps other than those listed in a claim or embodiment, "a" or "an" does not exclude a plurality, and a single feature or other unit may fulfil the functions of several units recited in the claims or embodiments. Any reference numerals or labels in the claims or embodiments shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A method comprising:
   with a headset in a known acoustic environment, applying an acoustic stimulus at a first transducer of the headset;
   receiving a response signal at a second transducer of the headset, the response signal comprising a component of the acoustic stimulus reflected at an obstacle in the acoustic path of the first transducer;
   determining a condition of the headset based on the response signal; and
   performing a noise cancelling process based on the determined condition.

2. The method of claim 1, wherein the known acoustic environment is a charging case of the headset or an ear of a user.

3. The method of claim 1, wherein the obstacle comprises a transducer grille.

4. The method of claim 1, wherein the condition comprises a blockage in the acoustic path.

5. The method of claim 1, wherein determining the condition comprises comparing the response signal to a template response signal.

6. The method of claim 5, wherein the template response signal represents an optimal condition of the acoustic path or a previous condition of the acoustic path.

7. The method of claim 5, wherein determining the condition further comprises extracting one or more features of the response signal, and wherein comparing the response signal to the template signal comprises:
   comparing each of the extracted features with a corresponding template feature, the corresponding template features representing the optimal condition of the acoustic path or the previous condition of the acoustic path.

8. The method of claim 1, wherein performing a noise cancelling process based on the determined condition comprises:
   adjusting one or more parameters of a cancellation filter configured to cancel noise associated with the determined condition.

9. The method of claim 8, further comprising:
   pre-filtering, by the cancelation filter, a signal output of the first and/or second transducer to remove noise associated with the determined condition.

10. The method of claim 1, wherein performing a noise cancelling process based on the determined condition comprises:
    adjusting one or more parameters of an active noise cancellation (ANC) system.

11. The method of claim 10, wherein the ANC system is configured to implement: (i) feedforward ANC; (ii) feedback ANC; or (iii) feedforward ANC and feedback ANC.

12. The method of claim 10, wherein the ANC system is configured to implement feedforward ANC and feedback ANC, and wherein the method further comprises:
    determining the condition of the headset based on the response signal as being aversive; and
    switching off the feedback ANC of the ANC system.

13. The method of claim 12, further comprising:
implementing a relatively less aggressive filter of the ANC system.

14. The method of claim 1, wherein (i) the first transducer is a loud speaker; (ii) the second transducer is a microphone; or (iii) the first transducer and the second transducer are the same transducer.

15. An apparatus, comprising processing circuitry and a non-transitory machine-readable which, when executed by the processing circuitry, cause the apparatus to:
with a headset in a known acoustic environment, apply an acoustic stimulus by a first transducer of the headset;
receive a response signal at a second transducer of the headset, the response signal comprising a component of the acoustic stimulus reflected at an obstacle in the acoustic path of the first transducer;
determine a condition of the headset based on the response signal; and
perform a noise cancelling process based on the determined condition.

16. The apparatus of claim 15, comprising:
the first transducer; and
the second transducer.

17. The apparatus of claim 16, wherein the first transducer is a loud speaker and wherein the second transducer is a microphone.

18. The apparatus of claim 15, comprising an ANC system.

19. An electronic device, comprising the apparatus of claim 15.

20. A non-transitory machine-readable medium storing instructions which, when executed by one or more processors, cause an electronic apparatus to:
with a headset in a known acoustic environment, apply an acoustic stimulus at a first transducer of the headset;
receive a response signal at a second transducer of the headset, the response signal comprising a component of the acoustic stimulus reflected at an obstacle in the acoustic path of the first transducer;
determine a condition of the headset based on the response signal; and
perform a noise cancelling process based on the determined condition.

* * * * *